US006228654B1

(12) United States Patent
Chait et al.

(10) Patent No.: US 6,228,654 B1
(45) Date of Patent: *May 8, 2001

(54) METHODS FOR STRUCTURE ANALYSIS OF OLIGOSACCHARIDES

(75) Inventors: Brian T. Chait; Ying-Ming Zhao, both of New York, NY (US); Stephen B. H. Kent, La Jolla, CA (US)

(73) Assignees: The Scripps Research Institute, LaJolla, CA (US); The Rockefeller University, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/647,405

(22) Filed: May 9, 1996

(51) Int. Cl.[7] .............................. G01N 33/48; B01D 59/44
(52) U.S. Cl. ........................... 436/94; 436/173; 436/175; 250/281; 250/282
(58) Field of Search ............................... 430/94, 95, 173, 430/175, 183; 250/281, 282, 287, 288

(56) References Cited

U.S. PATENT DOCUMENTS

| 5,045,694 | 9/1991 | Beavis et al. ...................... 250/287 |
| 5,470,949 | 11/1995 | Polt ...................................... 530/322 |

FOREIGN PATENT DOCUMENTS 5-339262 * 12/1999 (JP) .
9425071 * 11/1994 (WO) .

OTHER PUBLICATIONS

Canne et al. (1995) J. Am. Chem. Soc. 117:2998–3007.
Cervigni et al. (1996) Agnew. Chem. Int. Ed. Engl. 35:1230–2.
Edge et al. (1992) Proc. Natl. Acad. Sci. USA 89:6338–42.
Kurth et al. (1993) J. Med. Chem. 96:1255–61.
Mikola et al. (1992) Bioconjugate Chem. 3:182–6.
Rose, K. (1994) J. Am. Chem. Soc. 116:30–3.
Shao et al. (1995) J. Am. Chem. Soc. 117:3893–9.
Sutton et al. (1994) Analyt. Biochem. 218:34–46.
G. Sosnovsky et al. *Synthesis* 1979, 722–724.*
A. Fernandez–Mayoralas et al. *Tetrahedron* 1988, 44, 4877–4882.*
A. K. Jain et al. *J. Chem. Soc. Perkin Trans. 2* 1989, 153–157.*
H. Hettler et al. *Tetrahedron Lett.* 1966, 6031–6035.*
H. Schweer *J. Chromatog.* 1982, 236, 355–360.*
M. Jankovsky et al. *Chem. Abstr.* 1985, 103, 69873z.*
A.R. Long et al. *J. Food Sci.* 1987, 52, 150–154.*
D.J. Harvey *Rapid Commun. Mass. Spectrom.* 1993, 7, 614–619.*
M.C. Huberty et al. *Anal. Chem.* 1993, 65, 2791–2800.*
S. Tisza et al. *J Chromatog, A* 1994, 676, 461–468.*
M. Kanai et al, *Chromatography* 1995, 16, 23–30.*
P. Juhasz et al *Carbohydr. Res.* 1995, 270, 131–147.*
M. Okamoto et al. *Chromatography* 1995, 10, 326–327.*
R. M. Whittal et al. *Anal. Chem.* 1995, 67, 3509–3514.*
K. Yoshino et al. *Anal. Chem.* 1995, 67, 4028–4031.*
Y. Yang et al. *Anal. Chem* 1996, 68, 570–572.*
Shriner, R.L., et al., *The Synthetic Identification of Organic Compounds, A Laboratory Manual*, 5th ed., John Wiley & Sons, Inc. New York (1964) 289–290.
Fieser, L.F. et al., *Textbook of Organic Chemistry*, D.C. Heath & Co., Boston (1950) 206–209.

* cited by examiner

*Primary Examiner*—Arlen Soderquist
(74) *Attorney, Agent, or Firm*—Welsh & Katz, Ltd.

(57) ABSTRACT

A method of increasing the sensitivity and efficiency of MALDI-MS analysis of an oligosaccharide which comprises derivatization, prior to analysis by MALDI-MS, of said oligosaccharide by efficient ligation to a basic aminooxyacetylpeptide by oxime formation reaction to result in the formation of a glycoconjugate.

7 Claims, 4 Drawing Sheets

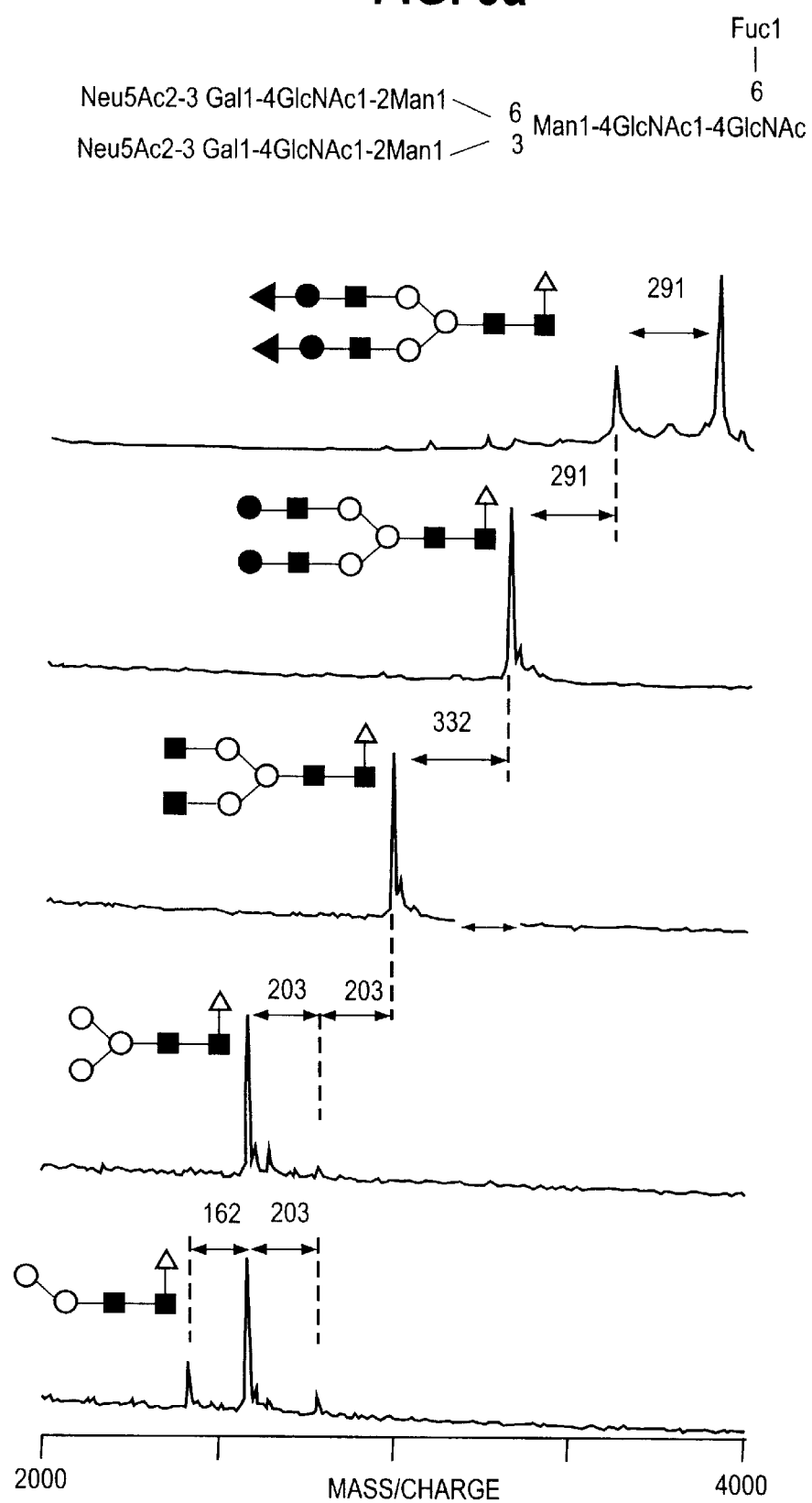

SEQUENCE LISTING

```
<160> NUMBER OF SEQ ID NOS:  7

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 1

Lys Leu Glu Glu Gln Arg Pro Glu Arg Val Lys Gly
  1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 2

Ala Leu Asp Glu Ala Arg Pro Glu Arg Gly Lys
  1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 3

Gly Asp Ala Arg Lys Pro Val Glu Arg Gly Lys
  1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 4

Gly Glu Ala Arg Lys Ala Val Glu Arg Asp Lys
  1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 5

Ala Val Thr Arg Val Ser Val Glu Lys Ala Lys
  1               5                  10
```

```
<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 6

Val Ala Ser Lys Asp Thr Val Glu Lys Ala Lys
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Related to
      human translationally controlled tumor protein

<400> SEQUENCE: 7

Ala Val Lys Ser Asp Thr Val Lys Arg Ala Val
 1               5                  10
```

METHODS FOR STRUCTURE ANALYSIS OF OLIGOSACCHARIDES

BACKGROUND OF THE INVENTION

Figure 1A:
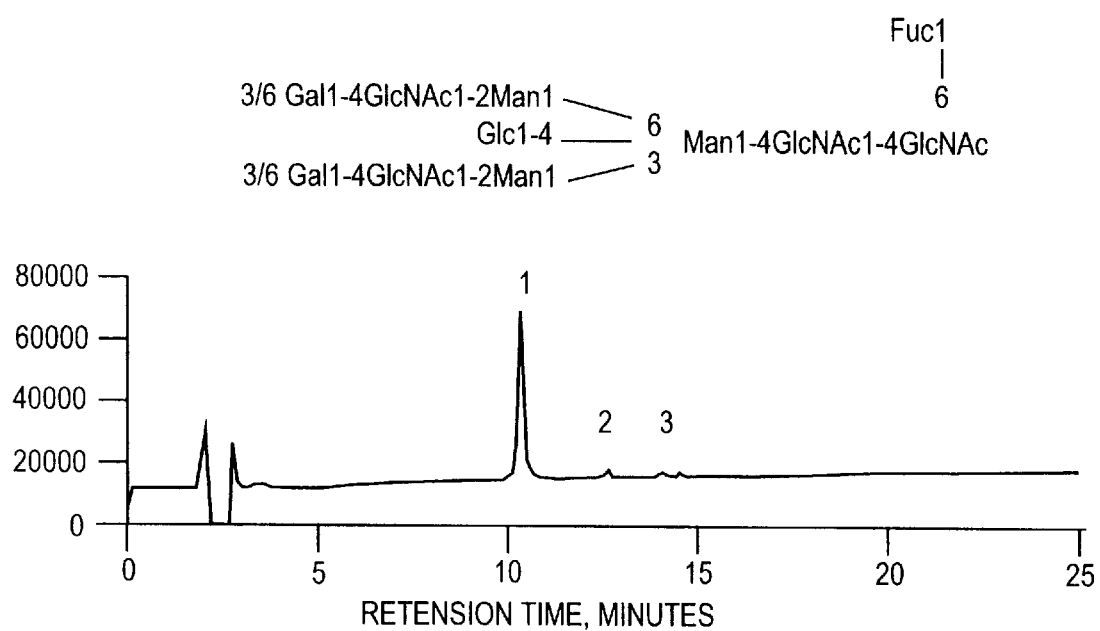

Over the past few years, mass spectrometry, and especially matrix-assisted laser desorption/ionization mass spectrometry (MALDI-MS), has been proved to be a vary valuable tool for the structural analysis and characterization of biological macromolecules, such as polypeptides, nucleic acids and oligosaccharides. Nevertheless, application of mass spectrometry, especially MALDI-MS, to the structure analysis of oligosaccharides presents greater challenges than the analysis of polypeptides. The difficulty originates from the intrinsic complexity of oligosaccharide structures and the generally poor response of carbohydrates to standard MALDI, which lead to low sensitivity of the measurement.

During positive ion MALDI, a sample molecule is usually ionized as a protonated ion. Basic groups (such as the side chains of lysine, arginine and histidine in peptides) of the analyte facilitate ionization processes through their strong proton affinity. However, the neutral and acidic oligosaccharides lack basic groups and are usually ionized with lower efficiency by alkali metal cationization when small amount of salts are present). The resulting low sensitivity of oligosaccharides has heretofore limited the application of MALDI for the structure analysis of oligosaccharides.

A variety of derivatization methods for oligosaccharides have been developed to increase the sensitivity of mass spectrometric analysis. Most of these methods use reductive amination. Such procedures usually involve the formation of a covalent linkage by the reduction of a Schiff's base adduct between a primary amine and an acyclic aldehyde or ketone form of the oligosaccharide. This type of derivatization can provide a basic moiety for protonization during ionization, but often result in incomplete reactions, and consequently a multiplicity of products.

Accordingly, it is a principal object of the present invention to provide a method for derivatization of oligosaccharides to facilitate their structure analysis by MALDI.

It is a further object of the present invention to provide a method as aforesaid which is characterized by the derivatization of an oligosaccharide by efficient ligation to a basic aminooxyacetyl peptide by oxime formation reaction, resulting in the formation of a glycoconjugate which yields higher sensitivities in MALDI-MS than the corresponding underivatized oligosaccharide.

It is a further object of the present invention to provide a glycoconjugate derivative of an oligosaccharide which affords an efficient mechanism for the mass determination of oligosaccharides (using mass spectrometry, especially MALDI-TOF MS or ESI MS), as well as fragmentation information from collision-induced dissociation (CID) experiments in the mass spectrometry, especially the MALDI-ITMS instrument.

It is a yet further object of the present invention to provide a method by which digestion of the glycoconjugate derivative by glycosidase arrays in combination with mass spectrometric assay of the digests present a sensitive and rapid approach to elucidation of oligosaccharide linkages, sequence and branching.

It is a still further object of the present invention to provide a faster method than the column chromatography or gel-electrophoresis currently used in commercial oligosaccharide analysis which method can be utilized with impure oligosaccharides, due to the higher resolution of MALDI-MS over column chromatography or gel-electrophoresis.

It is yet another object of this invention to provide a method wherein incomplete glycosidase digestion is acceptable since the structure information of an oligosaccharide is obtained from molecular weight difference, specificities and composition of glycosidase mixture.

It is a further object of the present invention to provide a method of analysis for oligosaccharides wherein the sensitivities is very high, even with the use of picomolar quantities of sample.

It is a still further object of the present invention to provide a method of synthesizing glycoproteins using the novel reaction sequence of the instant invention.

Other objects and advantages will become apparent to those skilled in the art from a consideration of the ensuing description which proceeds with reference to the following illustrative drawings.

BRIEF DESCRIPTION OF THE DRAWING FIGURES

FIG. 1A is an RP-HPLC analysis of the ligation reaction products. Peak 1: Glycopeptide; peaks 2 and 3 are side products formed between the aminooxyacetyl peptide with formaldehyde and acetone respectively. Identities of the peaks were confirmed by mass spectrometric analysis of HPLC fractions. HPLC conditions are as described in the Examples below. Yield of the ligation reaction in the figure was calculated from peak intensities of HPLC.

Figure 1B:
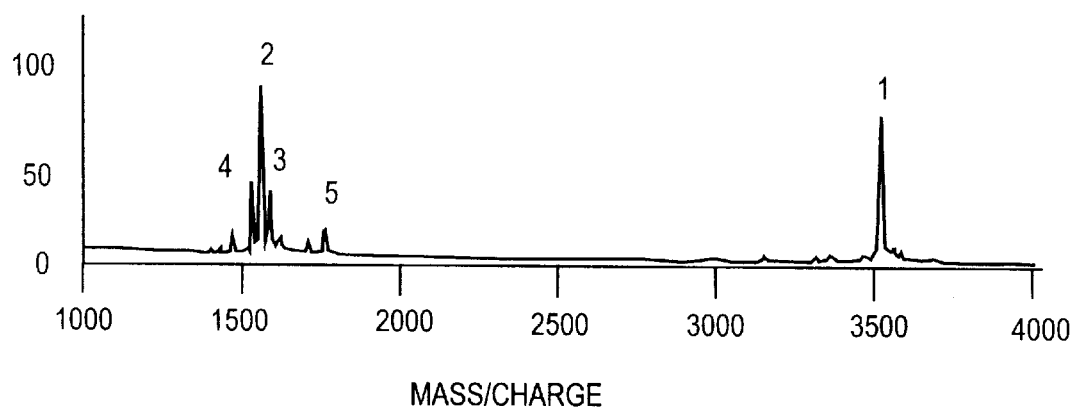

FIG. 1B is a mass spectrometric analysis of the ligation reaction products. The experiment was carried out on a MALDI-TOF mass spectrometer. The peak 1, 2, and 3 in the mass spectrum corresponds to fractions 1, 2, 3 in (A). Peak 4 is a fragment ion produced through breakage of N—O bond of reaction products during MALDI-MS processes. Yield of the ligation reaction in the figure was calculated from peak intensities of HPLC.

Figure 2A:
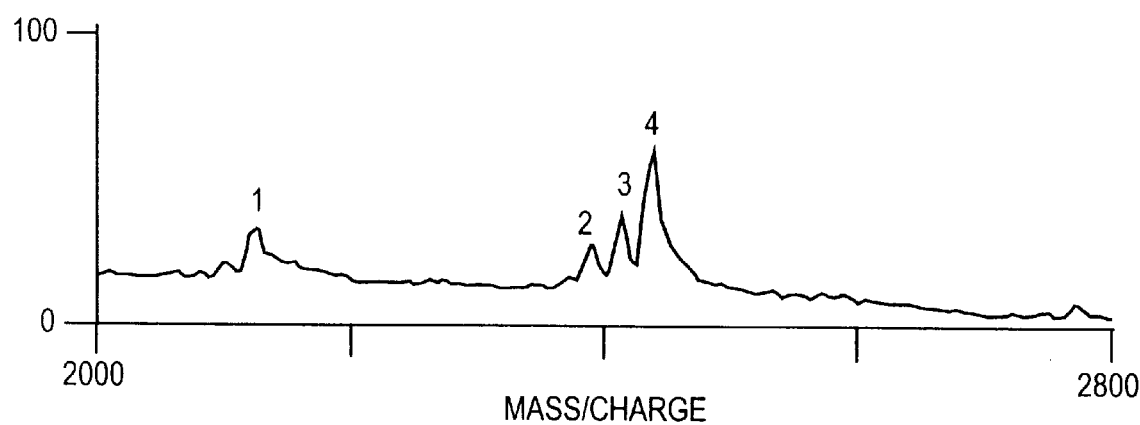
Figure 2B:
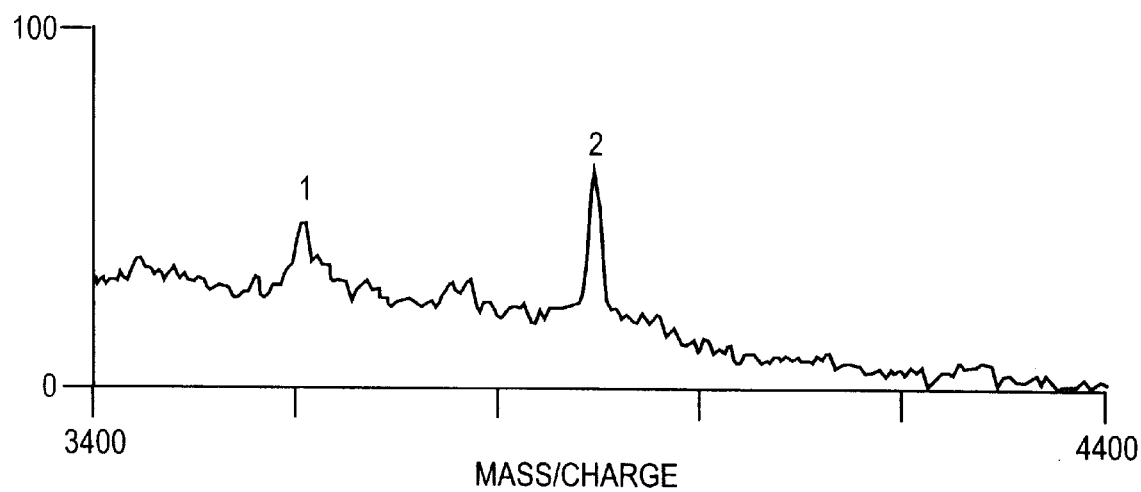

FIG. 2 is a comparison of the sensitivities of derivatized and underivatized A2F oligosaccharide. The MALDI mass spectrum of underivatized A2F is shown in FIG. 2A, and that of derivatized A2F is shown in FIG. 2B. (A): 0.2M 2,5-dihydroxybenzoic acid (DHB): 0.06M isocarbostyril (HIC) (1:1, v/v in acetonitrile:water 1:1) was used as matrix solution. 10 mM sodium chloride is present in the solution to obtain sodium adduct ions. The matrix analyte is dried under the vacuum in the sample probe. In addition to protonated peak 2, two sodium adduct peaks, 3 and 4, are observed. (B):Derivatized A2F was mixed with matrix solution (4-HCCA in ACN:0.1% TFA in water (1:1, v/v), loaded on the probe, and then dried at room temperature in air. Protonated glycopeptide ion is labeled by "2". Peaks for the side products of oxime formation reaction were present in low mass region. Peak label with "1" is ion signal for molecular ions with loss of one sialic acid. The experiment was carried out on a MALDI-TOF mass spectrometer. To prevent contamination from previous analysis, sample was diluted in new ependorf tubes and then loaded on a new sample probe. The sensitivity of derivatized A2F was calculated according to A2F used for derivatization reaction. Mass spectrometric analysis was performed without prior separation of glycopeptides from impurities, which are present in low mass region of mass spectra and does not interfere analysis.

Figure 3B:
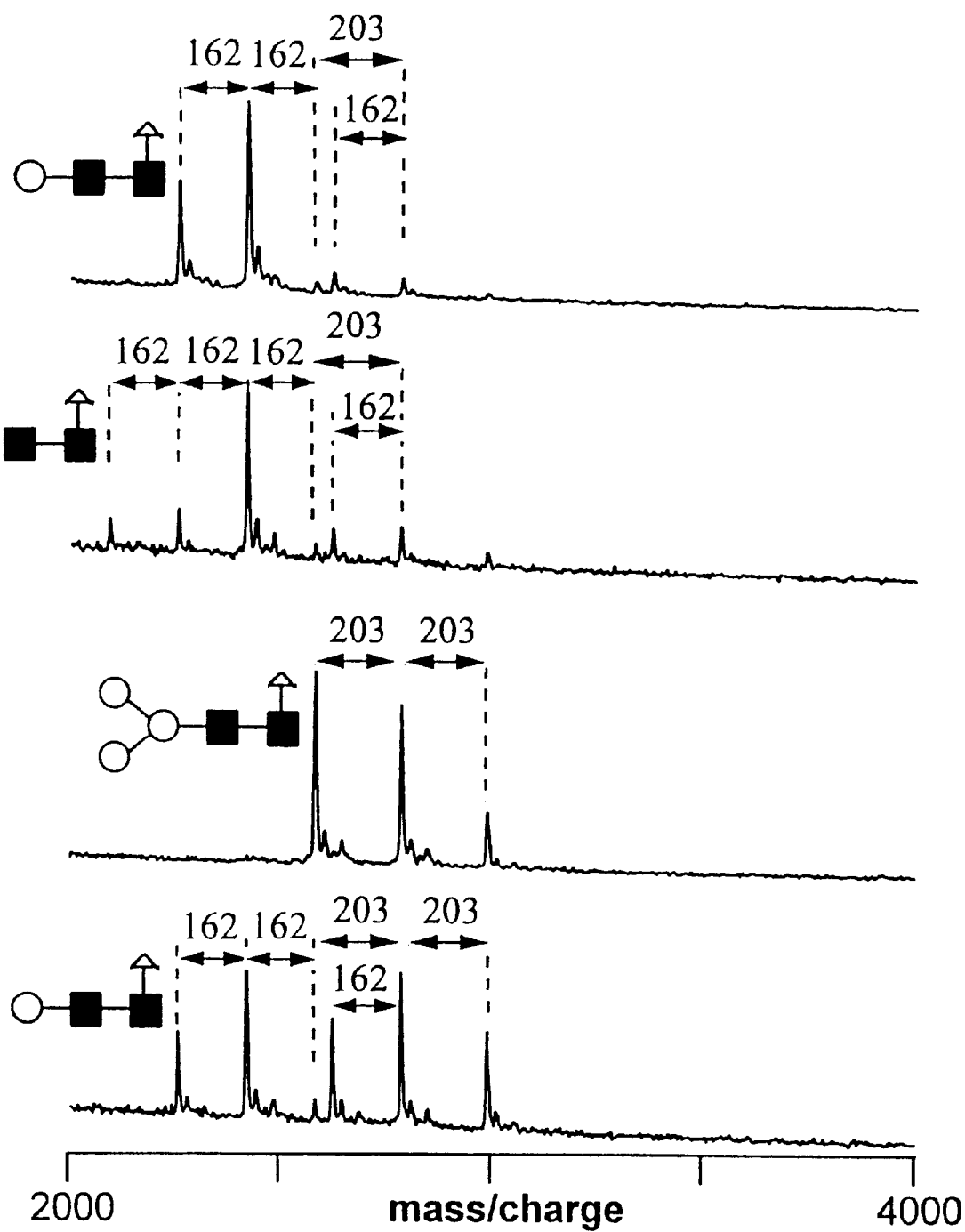

FIG. 3 is a diagram showing the ladder sequencing of a glycopeptide. A2F glycopeptide was divided into eight aliquots and digested by a series of glycosidase mixtures as described in Table 2. Mass interval of some digest peaks in mass spectra were indicated. Structures of some digestion products could be inferred from the mass differences. Monosaccharides are represented by symbols. Solid square—N-acetyl glucose; Solid circle—Galactose; Open circle—Mannose; Open triangle—Fucose; Solid triangle—Sialic acid.

SUMMARY OF THE INVENTION

The present invention involves a method for the derivatization of oligosaccharides to facilitate their structure analysis by matrix-assisted laser desorption/ionization mass spectrometry (MALDI-MS). More particularly, this invention relates to the derivatization of an oligosaccharide by efficient ligation to a basic aminooxyacetyl peptide by oxime formation reaction, resulting in the formation of a glycoconjugate which yields higher sensitivities in MALDI-MS than the corresponding underivatized oligosaccharide. The glycoconjugate derivative provides an efficient mechanism for the mass determination of oligosaccharides (using MALDI-TOF MS), as well as fragmentation information from collision-induced dissociation (CID) experiments in the MALDI-ITMS instrument. In addition, digestion of the glycopeptide derivative by glycosidase array in combination with mass spectrometric assay of the digests present a sensitive and rapid approach to elucidation of oligosaccharide linkages, sequence and branching.

The present invention also involves a method for synthesizing glycopeptides and glycoproteins using the step of ligating a highly reactive amine group at the N-terminal of an aminooxyacetyl peptide with an aldehyde group at the reducing end of a saccharide to form the intermediate oxime derivative.

DETAILED DESCRIPTION OF THE PREFERRED EMBODIMENTS

The amino acid residues described herein are preferred to be in the "L" isomeric form. However, residues in the "D" isomeric form can be substituted for any L-amino acid residue. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more aminoacid residues. The above Table is presented to correlate the three-letter and one-letter notations which may appear alternately herein.

The synthesis of the glycopeptide derivatives of the present invention takes advantages of the oxime formation reaction between a highly reactive amine group at the N-terminal of an aminooxyacetyl peptide and an aldehyde group at the reducing end of an oligosaccharide.

Selection of the peptide sequence for derivatization can vary according to the particular type of oligosaccharide being derivatized, but the peptide sequence is selected so as to provide a sequence which is soluble, highly basic, and preferably, having a mass of greater than 1200. These criteria result in oligosaccharide derivatives which can be analyzed with facility by mass spectrometry, and especially MALDI MS.

The derivatization reaction is modified from procedures for oxime formation described previously by Canne et al., *J. Am. Chem. Soc.*, (1995) 117, 2998–3007. In such a reaction sequence, the oligosaccharide is typically added to the aminooxyacetyl peptide in approximately equimolar ratios, preferably about 1:0.9 (oligosaccharide:aminooxyacetylpeptide), mixed with a polar, aprotic solvent, such as acetonitrile, dimethylformamide or dimethylsulfoxide, and incubated at 37° C. for a period of about 8–24 hours, preferably about 12 hours. The resulting reaction product is then dried in speed vacuum and redissolved in suitable amount of water. The reaction products can then be used for mass spectrometric analysis and glycosidase digestion without additional purification.

In this reaction, a basic peptide is used to increase the ionization efficiency of the resulting glycoconjugate in mass spectrometry. Particularly useful basic peptides for use in this reaction are those such as

| | |
|---|---|
| $H_2N$—O—$CH_2$CO-KLEEQRPERVKG | SEQ ID NO:1 |
| $NH_2$—O—$CH_2$CO-ALDEARPFRGK | SEQ ID NO:2 |
| $NH_2$—O—$CH_2$CO-GDARKPVERGK | SEQ ID NO:3 |
| $NH_2$—O—$CH_2$CO-GEARKAVERDK | SEQ ID NO:4 |
| $NH_2$—O—$CH_2$CO-AVTRVSVEKAK | SEQ ID NO:5 |
| $NH_2$—O—$CH_2$CO-VASKDTVEKAK | SEQ ID NO:6 |
| $NH_2$—O—$CH_2$CO-AVKSDTVKRAV | SEQ ID NO:7 |

The instant reaction is essentially specific for the aminooxyacetyl group, since no side reaction products are observed between the side chain of lysine and oligosaccharides.

Typical oligosaccharides which can be utilized in this reaction scheme can be any of the structurally diverse oligosaccharides including neutral, acidic, N-linkage and O-linkage oligosaccharides, such as A1, A2F, LSTa and NA2FB. Other oligosaccharides such as those derived from glycosylated proteins, such as mucins, and fibrogens, and glycolipids, protoglycans and glycosaminoglycans can also be derivatized and analyzed by the instant invention.

After successful ligation of the various oligosaccharides to the aminooxyacetylpeptide, the reaction mixture is separated by reverse-phase HPLC and the identities of the fractions were characterized by the molecular weights from mass spectrometry. The major side products were produced between the aminooxyacetylpeptide and impurities, such as formaldehyde, acetylaldehyde or acetone, typically present in reaction solvents such as acetonitrile and/or water. Generally, reaction yields were higher than 95%, indicating that the reaction is quite general and efficient.

The resulting glycopeptide conjugate produced by the instant process is quite stable, with no significant degradation being observed after incubation of the glycopeptide at 37° C. for 40 hours at pHs ranging from pH 4.3 to pH 8.0.

Once synthesized, the glycopeptide conjugate of the present invention can be subjected to MALDI-MS according to standard techniques known in the art. Such analysis provides a very high sensitivity, even with very small amounts of sample. Most advantageously, the reaction products can be used for mass spectrometric analysis and glycosidase digestion without additional purification.

In a standard analytical procedure, the oligosaccharide is first derivatized to the glycopeptide. Then, glycosidase digestion of the glycopeptide is typically conducted according to the reagent array analysis method described by Sutton et al. supra. In this approach, the structures of oligosaccharides are deduced from molecular weights of digestion products, composition and specificities of exoglycosidase mixture. Typical specificities and compositions of glycosidase mixtures are given in Table 1 below.

For underivatized oligosaccharides, 0.2 M DHB:0.06M HIC (1:1, v/v) in a solution (ACN:0.1% TFA in water (1:2, v/v)) turned out to be the best matrix when the analyte matrix solution was dried in the vacuum. DHB/MSA gave an ion signal similar to DHB/HIC.

Using a matrix-assisted laser desorption/ionization time-of-flight mass spectrometer, the spectra were taken using positive mode. Particular methodology and equipment for MALDI-TOF are well-known in the art, and are described, for example, in U.S. Pat. No. 5,045,694, whose teachings are herein incorporated by reference. Positive ion mass spectra were collected by adding individual spectra obtained from 100 laser shots. Table 2 below compares the sensitivities of various oligosaccharides prior to and after derivatization using the present method.

TABLE 2

| Sensitivity Enhancement after derivatization | | | | |
|---|---|---|---|---|
| Oligosaccharides | A1 | A2F | LSTa | NA2FB |
| Sensitivity before derivatization | 600 | 3000 | 10000 | 100–300 |
| Sensitivity after derivatization | 10 | 10 | 10 | 2 |
| Improvment | 60X | 300X | 1000X | 50–150X |

Specificities and Compositions of Glycosidase Mixtures

| Enzyme | Source | Linkage Specificity | Conc. (U/ml) | pH Optimum | Exoglycosidase Digests (no. of 0.5μ 1 aliquots) | | | | | | | |
|---|---|---|---|---|---|---|---|---|---|---|---|---|
| | | | | | A | B | C | D | E | F | G | H |
| Sialidase | Arthrobacter ureafaciens | α2-6 > 3,8 | 1 | 5.0–5.5 | 1 | 1 | 1 | 1 | 1 | 1 | 1 | 1 |
| Galactosidase | Streptococcus pneumonia | β1-4 | 0.2 | 5.5–6.5 | | 1 | 1 | 1 | 1 | 1 | 1 | |
| GlcNAcase | Chicken liver | β1-2,3,4,6 | 1 | 5.0–5.5 | | | 1 | 1 | 1 | 1 | | |
| GlcNAcase | Streptococcus pneumonia | β1-2 | 0.008 | 4.0–4.5 | | | | | | | 1 | 1 |
| Mannosidase | Jack bean | α1-3 | 0.1 | 4.0–4.5 | | | | 1 | | | | |
| Mannosidase | Jack bean | α1-2,3,6 | 5 | 4.0–4.5 | | | | | 1 | 1 | | 1 |
| Mannosidase | Helix pomatia | β1-4 | 1 | 4.0–4.5 | | | | | | | 1 | |
| sample | | | | | 1 | 1 | 1 | 1 | 1 | 1 | 1 | 1 |
| Buffer | 50 mM sodium citrate/phosphate, pH 5.0, 25 mM zinc chloride | | | | 1 | 1 | 1 | 1 | 1 | 1 | 1 | 1 |
| 10% Methanol | | | | | 7 | 6 | 5 | 4 | 4 | 3 | 5 | 4 |

The matrix compounds and procedures of sample preparation have significant influence on the ion response of analytes in MALDI-MS. Several commonly-used matrixes were evaluated for the purpose of improving the quality and sensitivity of mass spectra, including α-cyano-4-hydroxycinnamic acid (4-HCCA), 2,5-dihydroxy benzoic acid (DHB), 4-hydroxy-3-methoxycinnamic acid (FA), 3-hydroxypicolinic (HPA), 5-methoxysalicyclic acid (MSA), DHB/MSA, DHB/MSA/Fucose and DHB/ Isocarbostyril (HIC). Other matrix materials and those such as described in U.S. Pat. No. 5,045,694, which is herein incorporated by reference. In addition to matrixes, the sample preparation procedures, such as concentration of sodium chloride (for underivatized oligosaccharides), evaporation environment (in air or vacuum), and recrystallization conditions (using different organic solvents) can affect sensitivity of the overall analysis.

For a glycopeptide, the strongest ion signal was observed when the sample is dried at room temperature in air using 4-HCCA as matrix compound in a saturated solution (ACN:0.1% trifluoroacetic acid (TFA) in water (1:2, v/v)).

The present invention provides a successful method of ligating an oligosaccharide and aminooxyacetylpeptide. The resulting glycoconjugate is fifty to one thousand times more sensitive than underivatized carbohydrate in typical MALDI MS analysis. The glycoconjugate provides a very good reagent for CID experiment and glycosidase digestion for structure dissection. The sensitivity enhancement simplifies sample handling and promises to be very helpful when dealing with low-abundance oligosaccharides from biological sources.

In addition to mass spectrometry, there are several other approaches available for sequence analysis of oligosaccharides. They vary in methodology used, sensitivity, and structure information provided. One of the most commonly used method at present involves sequential removal of monosaccharide residues from oligosaccharides using exoglycosidases of high specificity. Edge et al., *Proc. Natl Acad Sci USA*, (1992) 89, pp.6338–6342 has refined this approach by judicious use of exoglycosidase arrays. In the approach, a labeled oligosaccharide is aliquoted and digested with multiple defined mixture of exoglycosidases to produce a list of "stop point" fragments from the original oligosaccharide. The end products of each reaction are pooled and then analyzed by column chromatography. The sequence and linkage information are deduced from the behavior of the digestion products in column chromatography. More recently, Sutton et al., *Analytical Biochemistry* (1994) 218, pp. 34–46 explored the usage of MALDI-MS for the analysis of digests from reagent array analysis method. In their approach, structures of oligosaccharides are deduced from molecular weights of digestion products, composition and specificities of exoglycosidase mixture.

These other sequence analysis procedures can likewise be enhanced by the usage of derivatized oligosaccharides for sequencing analysis by applying glycosidase digestion in combination with MALDI-TOF MS.

In addition to its use for oligosaccharide sequencing, the ligation reaction between an oligosaccharide and an aminooxyacetylpeptide also provides a very convenient and efficient synthesis for glycopeptides or glycoproteins for a number of other biomedical applications. An aminooxyacetyl group can be easily attached at the c-amino group of the side chain of lysine or directly structured in a modified amino acid residue, which can be introduced onto peptides during solid-phase or solution chemical peptide synthesis. Then, the oligosaccharide moiety can be ligated to the aminooxyacetyl peptide through the above-described oxime formation reaction. Although the resulting glycopeptide does not have the same linkage as natural one, it provides a very good approximation to a natural glycopeptide. A combination of glycopeptide synthesis with other protein ligations techniques such as those described by Canne et al., *J. Am. Chem. Soc.*, (1995) 117, 2998–3007; Shao et al., *J. Am. Chem. Soc.*, (1995)117, 3893–3899; and Rose, *J. Am. Chem. Soc.*, (1994) 11, 30–33 may also make it feasible for the synthesis of artificial proteins, glycopeptides and glycoproteins which would otherwise be difficult or impossible to manufacture.

This ligation reaction can be used for any sugar having a reducing end, i.e., a terminal sugar monomer with a reducible carbonyl group when the six member ring of the sugar is open.

Other potential applications of this method for the synthesis of glycopeptides or glycoproteins include the design of novel, non-naturally occurring glycoproteins, the preparation of oligosaccharide-based drug delivery dosage forms, the productions of vaccines and antibodies of oligosaccharide antigens, biosensors, and the engineering and production of glycopeptide or glycoprotein-based drugs. By utilizing the oxime formation reaction between the aldehyde or ketone of the oligosaccharide and an aminooxyacetyl group attached at the a-amino group of the side chain of lysine or directly structured in a modified amino acid residue, new and previously unknown glucopeptides and glucoproteins can be easily synthesized.

For instance, analogs of the glycoprotein, human transferrin, can easily be synthesized by such a route. Another useful product which is made synthetically available by this route is a high mannose glycopeptide of the formula

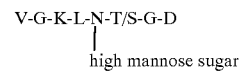

Such a reaction finds utility in the development of antibodies to the attached sugars, both polyclonal and monoclonal, since this reaction can be used to attach a sugar to modified bovine serum albumin (BSA) and the resultant glycoconjugate used as an immunogen to produce antibodies for the sugar.

Other derivatization reactions for the ligation between a peptide and an oligosaccharide which can be utilized in the practice of the instant invention to increase the sensitivity of the MALDI-MS analysis are those include the formation of a thiazolidine between a cysteine 1,2-aminothiol moiety of a peptide and an aldehyde or ketone group in a oligosaccharide; and the formation of a hydrazone between a hydrazide moiety of a peptide and an aldehyde or ketone group in a oligosaccharide.

Other objects and advantages will become apparent to those skilled in the art from a consideration of the ensuing description.

The following examples are illustrative of the invention.

EXAMPLE 1

Experimental Section

Materials

All the oligosaccharides and exoglysidase were purchased from Oxford GlycoSystems, Inc. (Albingdon, Oxon., UK). The procedures for preparation and storage of enzymes were followed the instructions from manufacturer. HPLC grade acetonitrile was purchased from Baxter Healthcare Co. (Muskegon, MI). a-Cyano-4-hydroxy-cinnamic acid (4-HCCA) was purchased from sigma Chemical Co. (St. Louis, Mo.). 2,5-dihydroxybenzoic acid and 1-hydroxy isocarbostyril (HIC) were purchased from Aldrich Chemical Company, Inc. Milwaukee, Wis.).

Peptide Synthesis

Aminooxyacetylpeptide (NH2—O—CH2CO—KLEEQRPERVKG) was synthesized by the stepwise solid-phase method. Purity and identity of the peptide was confirmed by HPLC and mass spectrometric analysis.

Synthesis of Glycopeptides

The derivatization reaction is modified from procedures for oxime formation described previously by Canne et al., *J. Am. Chem. Soc.*, (1995) 117, 2998–3007; Shao et al., *J. Am. Chem. Soc.*, (1995)117, 3893–3899; and Rose, *J. Am. Chem. Soc.*, (1994) 116, 30–33. Typically, 2 μl (20 to 200 pmol) of an oligosaccharide was added to 0.5 μl (18–180 pmol) of the aminooxyacetylpeptide with molar ratio 1:0.9 (oligosaccharide:aminooxyacetylpeptide), mixed with 47.5 μl of acetonitrile, and incubated at 37° C. for 12 hours. The resulting reaction product was dried in speed vacuum and redissolved in suitable amount of water. The reaction products were used for mass spectrometric analysis and glycosidase digestion without purification.

More than fifteen oligosaccharides including neutral, acidic, N-linkage and O-linkage oligosaccharides were successfully ligated to the aminooxyacetylpeptide. The reaction mixture was separated by reverse-phase HPLC and identities of fractions were characterized by the molecular weights from mass spectrometry. The major side products were produced between the aminooxyacetylpeptide and impurities, such as formaldehyde, acetylaldehyde or acetone, present in reaction solvents such as acetonitrile and/or water. Of the five reaction products analyzed by HPLC, reaction yields were higher than 95%, indicating that the reaction is quite general and efficient.

HPLC Analysis

Reverse-phase HPLC was carried out on a Microm HPLC system (Microm Bioresource, Inc., Pleasanton, Calif.) with 215 nm UV detection, using C-18 analytical (5 μm, 1×15 mm) column. Chromatographic analysis was performed using a linear gradient from 10% to 40% of buffer B in buffer A (A: 0.1% trifluoroacetic acid (TFA) in water (v/v); B: 90% $CH_3CN$ and 0.1% trifluoroacetic acid (TFA) in water (v/v)) in 20 minutes at μl/min.

Glycosidase Digestion of Glycopeptides

The glycopeptide was digested according to the procedures described by Sutton et al., *Analytical Biochemistry*, (1994) 218 pp. 34–36 except that the amount of each reaction volume was increased five times to 5 μl scale. Typically, 8–40 pmol of a glycopeptide was divided in eight ependorf tubes and mixed with buffers and enzyme mixtures according to Table 1. The resulting solutions were incubated at 37° C. for about 20 hrs. Mix 2 μl of each digest with 2 μl of 4HCCA, load 1.5 μl of the resulting solution on sample probe for MALDI-TOF mass spectrometric analysis.

Mass Spectrometric Analysis

Except for the collision-induced dissociation (CID) experiment, all other mass measurement was carried out on a matrix-assisted laser desorption/ionization time-of-flight (MALDI-TOF) instrument constructed at the Rockefeller University. The spectra were taken using positive mode. Both positive ion mass spectra were collected by adding individual spectra obtained from 100 laser shots.

Matrix-assisted laser desorption laser desorption ion trap instruments

The matrix compounds and procedures of sample preparation had significant influence on the ion response of analytes in MALDI-MS. Several commonly-used matrixes were evaluated for the purpose of improving the quality and sensitivity of mass spectra, including α-cyano-4-hydroxy-cinnamic acid (4-HCCA), 2,5-dihydroxybenzoic acid (DHB), 4-hydroxy-3-methoxycinnamic acid (FA), 3-hydroxypicolinic (HPA), 5-methoxysalicyclic acid (MSA), DHB/MSA, DHB/MSA/Fucose and DHB/Isocarbostyril (HIC). In addition to matrixes, the sample preparation procedures, such as concentration of sodium chloride (for underivatized oligosaccharides), evaporation environment (in air or vacuum), and recrystallization conditions (using different organic solvents) were compared to afford the most sensitive analysis.

For a glycopeptide, the strongest ion signal was observed when the sample is dried at room temperature in air using 4-HCCA as matrix compound in a saturated solution (ACN:0.1% TFA in water (1:2, v/v)). For underivatized oligosaccharides, 0.2 M DHB:0.06 M HIC (1:1, v/v) in a solution (ACN:0.1% TFA in water (1:2, v/v)) turned out to be the best matrix when the analyte matrix solution was dried in the vacuum. DHB/MSA give a similar ion signal as DHB/HIC.

FIG. 2 compares detection limits of derivatized and underivatized oligosaccharide A2F in MALDI-TOF instrument. The sensitivity of mass measurement was increased for three-hundred fold after derivatization. Table 1 illustrates the sensitivity improvement of five oligosaccharides. The derivatization was found to increases sensitivity of mass measurement about fifty to one-thousand fold. For most of glycopeptides analyzed, sensitivities of the derivatized oligosaccharides are around low fmol rang, which is about the sensitivity limit for sample handling.

Typically, the sensitivity of MALDI-TOF mass spectrometric analysis quickly deteriorated when the molecular weight of an analyte goes below 800. Derivatization of an oligosaccharide with an aminooxyacetylpeptide not only attaches a basic peptide to the oligosaccharide but also pushes mass up by 1526 Da (mass of aminooxyacetylpeptide-18), a good range for mass spectrometric analysis. This advantage of the derivatives is most evident when small oligosaccharides or products from sequential exoglycosidase digestion are to be analyzed.

EXAMPLE 2

Ladder sequencing of a derivatized oligosaccharide

The derivatized oligosaccharides of the present invention can be utilized to enhance the sensitivity and results of glycosidase digestion sequence analysis in combination with MALDI-TOF MS. The digestion reactions were performed according to the procedure described by Sutton et al except that total volume of digestion buffer was increased from 1 μl to 5 μl for easy sample handling (see Table 2 above). A2F was used as an example to demonstrate the methodology. The derivatized oligosaccharide was used for digestion without prior separation from its side reaction products. The molecular weights of starting material and digestion products were measured by MALDI-TOF MS, and the results shown in FIG. 3. The structure information were obtained from (1): molecular weight of starting glycopeptide; (2): molecular weights of digestion products; (3): composition and specificities of exoglycosidases. The type of monosaccharide was determined by molecular weight difference. A 203, 299, 162 Da loss indicated the presence of HexNAc, sialic acid and hexose, respectively. The identities of monosaccharides and linkage were designated by specificities and composition of the glycosidase used.

MALDI-MS provides several advantages for assaying the digestion products from the enzyme array reagent procedure compared with the widely used commercial methods. First, MALDI-MS is much faster than the column chromatography or gel-electrophoresis currently used in commercial oligosaccharide analysis instrument. Analysis of eight samples of digestions can be completed in about one-half hour. Second, the present method is tolerant to impure oligosaccharides. Because MALDI-MS has much higher resolution than column chromatography or gel-electrophoresis, the impure oligosaccharides will not produce confusion in the analysis of data. By contrast, the commercial methods require relatively pure starting material. Third, incomplete glycosidase digestion is acceptable in the instant method since the structure information of an oligosaccharide is obtained from molecular weight difference, specificities and composition of glycosidase mixture. At times, incomplete digestion gives more structure information than complete digestion. This is because more "stop point" fragments are produced in incomplete digestion which result in more structure information. Finally, the sensitivity of this method is very high. Twenty pmole of sample can be easily analyzed by the instant technique.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of increasing the sensitivity and efficiency of mass spectrometry analysis of an oligosaccharide which comprises the steps of:

derivatizing said oligosaccharide by ligation to a basic aminooxyacetylpeptide by oxime formation reaction in a polar, aprotic solvent selected from the group consisting of acetonitrile, dimethylformamide and dimethylsulfoxide to result in the formation of a glycoconjugate; and analyzing said glycoconjugate with mass spectrometry.

2. A method according to claim 1 wherein said mass spectrometry analysis is matrix-assisted laser desorption/ionization mass spectrometry (MALDI-MS) analysis.

3. The method according to claim 2 wherein the basic aminooxyacetylpeptide of the derivatizing step is $H_2N$—O—$CH_2$CO-KLEEQRPERVKG SEQ ID NO:1).

4. A method according to claim 1 which further comprises digestion of the glycopeptide derivative by glycosidase array in combination with mass spectrometric assay of the digests to rapidly elucidate the oligosaccharide linkages, sequence and branching of the oligosaccharide under analysis.

5. A method according to claim 1 wherein said basic aminooxyacetylpeptide of the derivatizing step is $H_2N$—O—$CH_2$CO-KLEEQRPERVKG (SEQ ID NO:1).

6. A method of coupling a peptide to an oligosaccharide which comprises contacting the oligosaccharide with a peptide derivatized with an aminooxyacetyl group in approximately equimolar quantities in a polar, aprotic solvent selected from the group consisting of acetonitrile, dimethylformamide and dimethylsulfoxide.

7. A method of synthesizing a glycopeptide or glycoprotein which comprises contacting approximately equimolar quantities of a sugar having a reducing end, and a peptide or protein derivatized with an aminooxyacetyl group, in a polar, aprotic solvent selected from the group consisting of acetonitrile, dimethylformamide and dimethysulfoxide.

* * * * *